United States Patent [19]
Carmichael et al.

[11] Patent Number: 6,126,662
[45] Date of Patent: Oct. 3, 2000

[54] BONE IMPLANT

[76] Inventors: Robert P. Carmichael, 17 Austin Terrace, Toronto, On, Canada, M5R 1YZ; George K.B. Sandor, 12 Hill Crescent, Scarborough, Ont, Canada, M1M 1H9; Donald R. Johnson, 60 Rothean Drive, Whitby, Ontario, Canada

[21] Appl. No.: 09/199,323

[22] Filed: Nov. 25, 1998

[30] Foreign Application Priority Data

Oct. 9, 1998 [CA] Canada .................................... 2249902
Oct. 13, 1998 [CA] Canada .................................... 2249945

[51] Int. Cl.$^7$ .............................. A61B 17/68; A61C 8/00
[52] U.S. Cl. ................................ 606/72; 606/63; 433/173
[58] Field of Search .................................. 606/1, 53, 65, 606/72, 73, 104; 433/172–174

[56] References Cited

U.S. PATENT DOCUMENTS

| | | |
|---|---|---|
| 5,575,790 | 11/1996 | Chen et al. . |
| 5,672,176 | 9/1997 | Biedermenn et al. ..................... 606/65 |
| 5,704,939 | 1/1998 | Justin . |
| 5,766,009 | 6/1998 | Jeffcoat . |
| 5,899,940 | 4/1999 | Carchidi et al. . |
| 5,951,287 | 9/1999 | Hawkinson .............................. 433/173 |
| 5,961,329 | 10/1999 | Stucki-McCormick ................. 433/174 |

FOREIGN PATENT DOCUMENTS

| | | |
|---|---|---|
| 19822802 A1 | 11/1999 | Germany . |
| WO 96/35391 | 11/1996 | WIPO . |
| WO 99/01080 | 1/1999 | WIPO . |

OTHER PUBLICATIONS

ACE Dental Impant System—Mini–Catalog.
ACE Dental Implant System catalog entitled Osteodynamics and photographs and X–rays of procedures.
Albrektsson, T. A multicenter report on osseointegrated oral implants. The Journal of Prosthetic Dentistry, vol. 60, No. 1, pp.75–84, 1988.

Block, M.S., Chang, A., and Crawford, C. Mandibular alveolar ridge augmentation in the dog using distraction osteogenesis. The Journal of Oral and Maxillofacial Surgery. vol. 54,pp. 309–314, 1996.

Ilizarov, G.A. The tension–stress effect on the genesis and growth of tissues: Part I. The Influence of stability of fixation and soft tissue preservation. Clinical Orthopaedics and Related Research. Nr. 238, pp.249–285, 1989.

Ilizarov, G.A. The tension–stress effect on the genesis and growth of tissues: Part II. The influence of the rate and frequency of distraction. Clinical Orthopaedics and Related Reserach, Nr. 239, pp. 263–285, 1989.

Ueda, M., Sawaki, Y., and Oda, T. Ridge aumentation by distraction osteogenesis using osseointegrated implants. Abstract. The International Journal of Oral and Maxillofacial Implants. vol. 13, Nr. 2, pp. 289–290, 1998.

*Primary Examiner*—Michael Buiz
*Assistant Examiner*—William Lewis
*Attorney, Agent, or Firm*—Bereskin & Parr

[57] ABSTRACT

A kit of assemblable components for implantation into the bone of a mammal for use in distraction osteogenesis. The kit comprises a fixture, a footing and a distracter, the fixture including a longitudinally extending body portion with a proximal end and a distal end, the body portion having an exterior surface adapted for contact and integration with bone tissue, the body portion having a generally longitudinally extending bore extending from a proximal opening adjacent the proximal end to a distal opening adjacent the distal end. The footing includes a proximal surface and a distal surface. The distracter comprises a generally rod-shaped body including a distal end and a proximal end, and the proximal end of the distracter is adapted to bear against the footing. There are first and second engaging means on the fixture and the distracter respectively for adjustably locating the fixture relative to the distracter.

31 Claims, 10 Drawing Sheets

BONE IMPLANT

FIELD OF THE INVENTION

The present invention relates to the field of methods and devices for reconstructive surgery in the bones of mammals. In particular, the invention relates to surgery in connection with the bones of mammals to rebuild bone tissue. A particular application of the invention is the creation of a bone implant for use where anchoring and rebuilding of the bone is desired such as in reconstructive surgery of jaw bones. The invention will be discussed in the context of dental prostheses, although the technique and mechanism is applicable on a much broader scale.

BACKGROUND OF THE INVENTION

Osseointegration is defined clinically as the process whereby clinically asymptomatic rigid fixation of alloplastic materials is achieved and maintained in bone during functional loading. Discussion of this process is set out in the paper of Albrektsson, T. A multicenter report on osseointegrated oral implants. The Journal of Prosthetic Dentistry. Vol. 60, No. 1, pp. 75–84, 1988. Typical dental implants, when osseointegrated in the upper or lower jaw, provide stable anchorage for dental prostheses. One of the factors limiting the success of osseointegration is the quantity of host bone stock available at a given site. If a site has inadequate host bone it may not be possible to use typical implants, alternatively, the site will require augmentation. Need to generate bone volume may arise from different circumstances. The bone may have been inadequately formed at birth and thus there is a need to build up bone tissue to bring the bone structure closer to the norm. Bone may also have been lost as a result of trauma, disease or other factors. Sites with inadequate bone volume have heretofore been augmented in a variety of ways:

with autogenous bone grafted from a distant site in the body;

with freeze-dried allogeneic bone from a bone bank, or with bone substitutes such as coral granules or hydroxyapatite crystals.

Autogenous bone grafts have no risk of rejection or viral infection and provide vital progenitor cells. However, they usually require a general anesthetic and are accompanied by some degree of morbidity which may be unacceptable to the mammal involved, particularly where the patient is human. Freeze-dried bone is easily available but is unpredictable in its behaviour because it is devoid of vital progenitor cells, bone morphogenic protein, and other factors such as TG beta. It also carries with it the risk of viral transmission. Bone substitutes have similar problems.

Thus, in many cases there is a need to generate adequate bone volume at a particular site in the body. The present invention deals with a method and equipment to generate bone volume at a particular site. While the technique is applicable to increasing bone volume at any site in the body, the need for increased bone volume often arises in connection with the jaw of a human being. Where teeth have been lost through trauma, there is often accompanying damage in the upper or lower jaw bone. In many such cases, it will be desirable to use dental implants to anchor dental prostheses.

Heretofore, bone grafting, irrespective of source, has been carried out either prior to or concurrently with the placement of a dental implant when it is necessary to build up tissue of the upper or lower jaw. In either case, the procedure usually employs a membrane such as that sold under the trade mark GORTEX in a process called guided bone regeneration (GBR). While most configurations of bony defects are amenable to augmenting with GBR, it is widely acknowledged that defects in a jaw bone which are vertical in nature, in particular, are difficult to overcome.

A process called distraction osteogenesis was first described by Codivilla in 1904. The technique became popularized and was studied extensively by Ilizarov beginning in 1951. See in particular, the following publications of Ilizarov which also describe the work of Codivilla. Ilizarov, G. A. The tension-stress effect on the genesis and growth of tissues: Part 1. The influence of stability of fixation and soft tissue preservation. Clinical Orthopaedics and Related Research. Nr. 238, pp. 249–285, 1989 and Ilizarov, G. A., The tension-stress effect on the genesis and growth of tissues: Part II. The influence of the rate and frequency of distraction. Clinical Orthopaedics and Related Research. Nr. 239, pp. 263–285, 1989. In this process, growth of bone and healing of bone defects can be stimulated by pulling apart, or distraction, of bone segments. Ilizarov discovered that a cortical osteotomy, or corticotomy, which preserves the bone's medullary blood supply and preserves the overlying periosteum, when combined with slow distraction, permitted bone lengthening without a bone graft. More recently work has been carried out on dogs. This work has demonstrated that a vertical defect of a residual alveolar ridge of a jaw bone can be corrected using osseointegrated screw-shaped dental implants to anchor a distraction device. Block, M. S., Chang, A., and Crawford, C. Mandibular alveolar ridge augmentation in the dog using distraction osteogenesis. The Journal of Oral and Maxillofacial Surgery. Vol. 54, pp. 309–314, 1996. Furthermore, screw-shaped dental implants alone have been employed to elevate a rectangular osteotomy created in the jaw bone of dogs Ueda, M., Sawaki, Y., and Oda, T. Ridge augmentation by distraction osteogenesis using osseointegrated implants. Abstract. The International Journal of Oral and Maxillofacial Implants. Vol. 13, Nr. 2, pp. 289–290, 1998.

The foregoing references describe two separate and distinct procedures; firstly, osseointegration and secondly, the augmentation of bony defects by distraction osteogenesis. Moreover, during the movement of bone in the direction of distraction, as disclosed in this prior work, the implant is continuously turned in the segment of bone being moved, with integration of the implant occurring only after distraction has been completed.

The use of dental implants in jaw bones where there is no need to augment the existing bone structure is now well-known. Various forms of implant have been created which rely on the growth of bone tissue in and around the implant to create a long lasting, mechanical union between the implant and the natural supporting bone. It is well-known that two primary bonding mechanisms can effect such osseointegration. These are microscopic bonding between the bone tissue and the implant surface and macroscopic ingrowth of bone into interstices of the implant to create a mechanical locking effect. One recent patent discussing such implants is U.S. Pat. No. 5,766,009 issued Jun. 16, 1998 entitled Elastically Stabilized Endosseus Dental Implant.

Thus, there is now a body of knowledge relating to the use and integration of dental implants. Some work has been done in the field of distraction osteogenesis. The two fields have been worked in independently.

Accordingly, within the field of orthopaedics it would be desirable to have a device which enables osteogenesis to occur by distraction to rebuild bone tissue at a particular site. It would also be desirable to have a distraction device which may serve as an anchor for a prostheses following completion of the distraction osteogenesis. This would reduce risk, discomfort and overall cost to the patient.

SUMMARY OF THE INVENTION

The present invention provides a kit of assemblable components for implantation into the bone of a mammal for use in distraction osteogenesis. The kit comprises a fixture, a footing and a distracter, the fixture including a longitudinally extending body portion with a proximal end and a distal end, the body portion having an exterior surface adapted for contact and integration with bone tissue, the body portion having a generally longitudinally extending bore extending from a proximal opening adjacent the proximal end to a distal opening adjacent the distal end. The footing includes a proximal surface and a distal surface. The distracter comprises a generally rod-shaped body including a distal end and a proximal end, and the proximal end of the distracter is adapted to bear against the footing. There are first and second engaging means on the fixture and the distracter respectively for adjustably locating the fixture relative to the distracter.

In a preferred embodiment the kit also includes an obturator. In a further preferred embodiment, the kit includes an obturator and a retaining screw.

The preferred embodiment illustrated in the drawings is intended for use as a dental implant to be placed in either the upper or lower jaw. The structure and method involved in this invention however may be used in any bone of any mammal where it is desired to rebuild bone using the procedure of distraction osteogenesis. Accordingly, the orientation of the device is not restricted. For purposes of describing the preferred embodiment illustrated herein, the terms "distal", "proximal" and "direction of distraction" will be used to indicate relative orientation and movement of the parts. The term "proximal" will be used with reference to the bone involved while the term "distal" will be used to describe that surface or direction which is remote from the centre of the bone.

Figure 1:
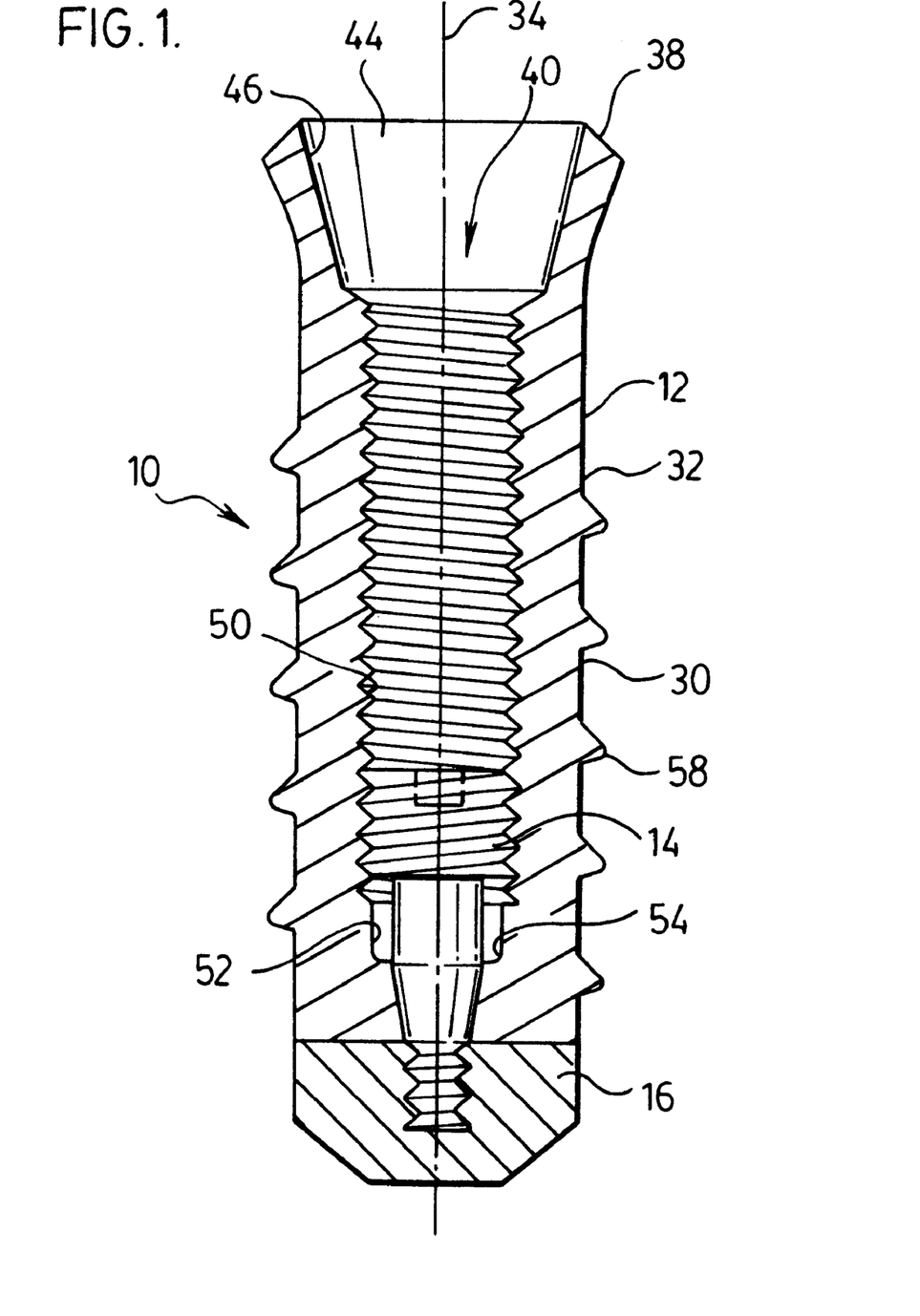
FIG. 1 is a cross-sectional view of an assembly of components of a dental implant ready for initial implantation and made in accordance with a preferred embodiment of the invention illustrating three component parts.

FIG. 1 illustrates an assembly of the device in accordance with this embodiment of the invention, the assembly being connected together in the configuration ready for implantation into the jaw bone. As shown in FIG. 1, the orientation is such that the assembly can be considered to be ready for implantation in a lower jaw and the direction of distraction will be vertically upwardly in these figures. It will be realized after appreciating this invention however, that the direction of distraction need not be vertical and may be in any direction relative to the bone being augmented, depending upon the surgeon's needs and the ongoing use to be made of the remaining implant.

The assembly shown in FIG. 1 generally at 10 comprises a fixture 12, a retaining screw 14 and a footing 16. The fixture 12 is shown in cross-sectional view in FIG. 2. The footing 16 is illustrated in cross-section in FIG. 3 and the retaining screw 14 is illustrated in FIG. 4.

Figure 5:
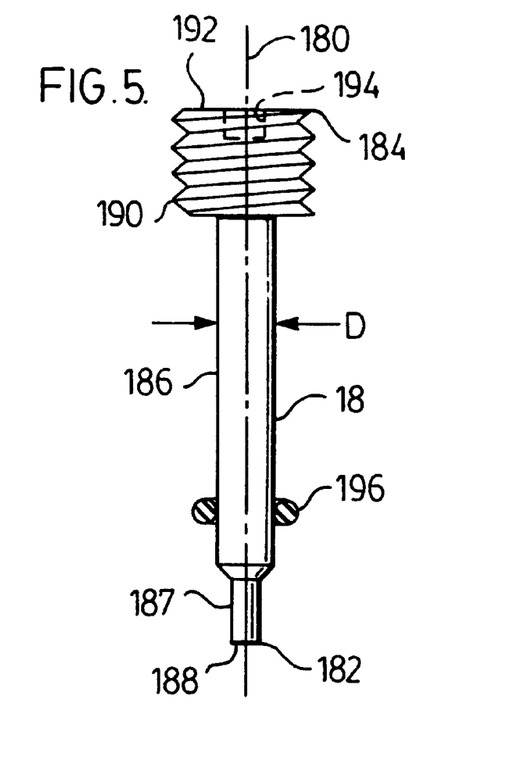
FIG. 5 illustrates a component for use with the components of FIGS. 2 and 3.

FIG. 5 illustrates a distracter 18 for use with the fixture 12 and the footing 16.

Figure 6:
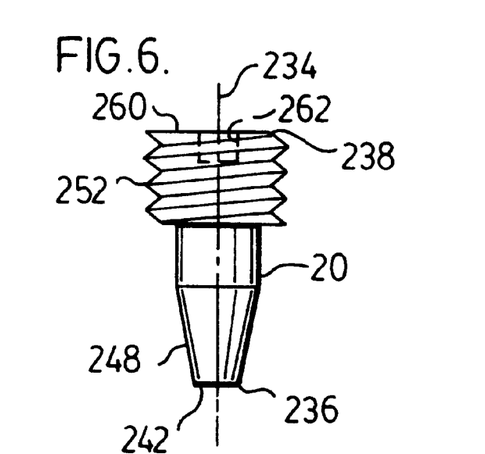
FIG. 6 illustrates a further component for use with the components of FIGS. 2 and 3.

FIG. 6 illustrates an obturator 20 for use with the fixture 12.

Figure 2:
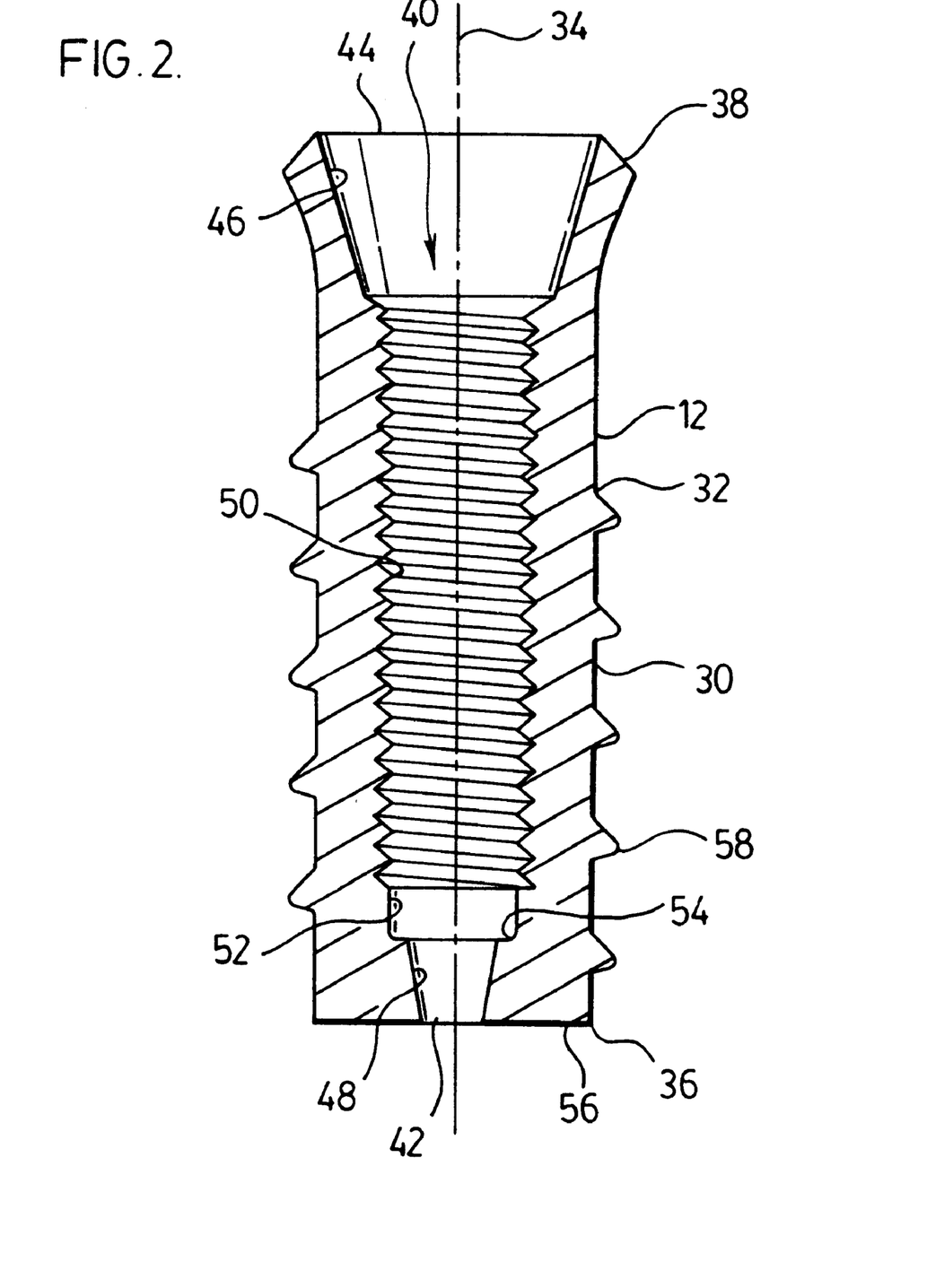
FIG. 2 illustrates one of the components of the assembly of FIG. 1.

The fixture 12 has a body portion 30 having an external surface 32. The body portion is generally cylindrical having a central axis 34. The body portion 30 has a proximal end 36 and a distal end 38. The body portion 30 has a generally centrally located bore 40 substantially centered on axis 34. The bore 40 extends substantially through the body portion 30 of the fixture 12 from a proximal opening 42 at the proximal end 36 to the distal opening 44 at the distal end 38. The bore 40 includes a distal tapered surface 46 which tapers inwardly from the distal opening 44 toward the axis 34. The bore 40 also has a proximal tapered surface 48 which tapers outwardly from the proximal opening 42 with respect to the axis 34.

The bore 40 of the fixture 12 further includes a first interengaging means 50 for adjustably locating the fixture 12 with respect to the distracter 18. In addition, the first interengaging means 50 for adjustably locating the fixture relative to the distracter may also be used to locate the fixture 12 relative to the retaining screw 14.

As shown in the preferred embodiment in FIGS. 1 and 2, the first interengaging means 50 for adjustably locating the fixture relative to the distracter comprises a helical thread extending a substantial portion of the length of the bore 40.

The bore 40 of the fixture 12 further includes a cylindrical surface 52 which merges with the tapered surface 48 at a land 54.

The fixture 12 has a proximal surface 56. As shown, the surface 56 is preferably planar but may have other shapes as desired.

The external surface 32 of the fixture 12 is adapted to promote osseointegration of the fixture 12 with surrounding bone tissue of the mammal. The surface may be treated in various ways to promote the osseointegation. This may be done by micro etching the surface or in any other way as is commonly used with prior dental implants and the like. In this case the surface is provided with a rib 58 which projects outwardly from the surface 32 relative to the axis 34. The rib 58 advantageously comprises a spiral which extends down the body portion 30 to form what is in effect a thread extending substantially over the length of the body portion 30. The thread thus provides a mechanical fixation for ingrowth of bone and more secure integration of the fixture 12 with the bone.

Figure 3:
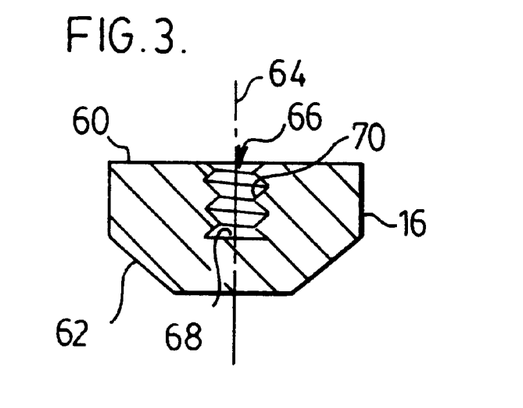
FIG. 3 illustrates a second component of the assembly of FIG. 1.
Figure 4:
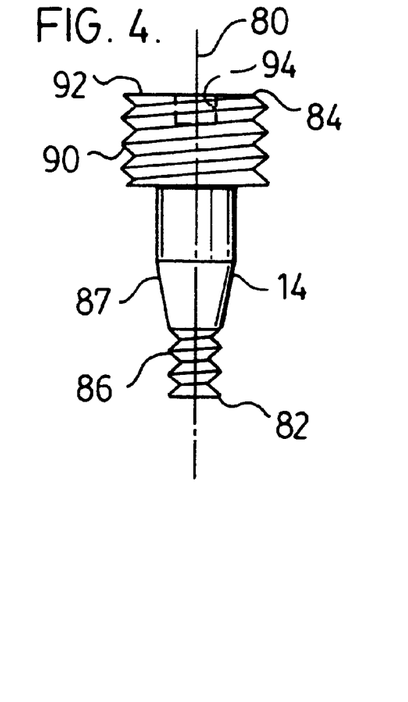
FIG. 4 illustrates a third component of the assembly of FIG. 1.

The footing 16 is illustrated in cross-section in FIG. 3. The footing 16 has a distal surface 60 which is preferably planar and a proximal surface 62. The footing is substantially saucer-shaped and is substantially symmetrical about a central axis 64. The footing 16 comprises a bore 66 which is generally concentric with axis 64. The bore 66 extends longitudinally inwardly from the distal surface 60 but does not penetrate proximal surface 62. The bore 66 has a bottom surface 68. The bore 66 comprises a threaded surface 70 for engagement with the retaining screw 14.

The retaining screw 14 is illustrated in FIG. 4. The retaining screw 14 has a generally elongate body which is generally symmetrical about a substantially centrally located axis 80. The retaining screw 14 has a proximal end 82 and a distal end 84. At the proximal end 82, the retaining screw 14 comprises a threaded surface 86. The threaded surface 86 has threads which are complimentary to the threaded surface 70 of the footing so that the threaded surface 86 will be received within the threaded surface 70 of the footing. In addition, the retaining screw 14 includes a tapered portion 87 adjacent the threaded surface 86. The tapered portion 87 is tapered complimentary to the tapered surface 48 of the fixture 12 so that in use a seal will be obtained between surfaces 48 and 87 for purposes explained below. When the retaining screw 14 is fully inserted into the fixture 12 the threaded surface 86 of the retaining screw 14 projects through the proximal opening 42 of the fixture 12.

Adjacent the distal end 84 of the retaining screw 14, is an interengaging means 90. The interengaging means 90 comprises a thread which extends along the exterior surface of the retaining screw 14 at the distal end 84. The diameter and configuration of the interengaging means 90 cooperates with the first inter engaging means 50 of the fixture 12. Thus, the threads 50 and 90 comprise first and second interengaging means on the fixture 12 and on the retaining screw 14 respectively, for adjusting the relative location of the retaining screw 14 relative to the fixture 12.

At the distal end 84 of the retaining screw 14 there is generally planar surface 92. A socket 94 is located in the planar surface 92 with the socket being substantially centrally located with respect to the axis 80.

The socket 94 may be shaped in any convenient configuration to receive a tool so that the retaining screw 14 may be rotated by means of a tool inserted into the socket 94. Socket 94 may be a simple slot for use with a blade type screwdriver. Preferentially however, the socket is polygonal shaped such as either hexagonal or octagonal and the tool used to rotate the socket may be in the nature of an Allan key or the like.

To create the assembly shown in FIG. 1, the retaining screw 14 is placed within the bore 40 of the fixture 12. The thread 90 will interengage with the thread 50. A tool is then inserted in socket 94 and the retaining screw rotated relative to the fixture 12. Rotation is continued until the proximal end 82 passes through the proximal opening 42. Rotation is continued until the tapered surface 87 seals against the tapered surface 48 of the fixture 12. At that point, a few of the threads 86 of the retaining screw 14 project beyond the proximal surface 56 of the fixture 12. The footing 16 may then be placed against the retaining screw 14. By rotation of the footing relative to the fixture 12 the threaded surface 70 of the footing 16 will engage with the threaded surface 86 of the retaining screw 14. The footing 16 is rotated relative to the retaining screw until the distal surface 60 is located substantially adjacent to and preferably in contact with the proximal surface 56 of the fixture 12. This completes the assembly as shown in FIG. 1, there being no substantial space between the proximal surface 56 of the fixture 12 and the distal surface 60 of the footing 16. In the assembled configuration, axes 34, 64 and 80 are aligned.

FIG. 5 illustrates the distracter 18. The distracter 18 has a generally rod-shaped body and is generally symmetrical about a central axis 180. The distracter 18 has a proximal end 182 and a distal end 184.

Adjacent the proximal end 182 of the distracter 18 is a bearing surface 188. The distracter 18 comprises a generally cylindrical portion 186 having a diameter D extending to adjacent the proximal end 182 of the distracter 18. At the proximal end 182, the distractor 18 includes a cylindrical surface 187 of reduced diameter as compared to diameter D. The reduced diameter of surface 187 is such that the cylindrical surface 187 may pass into the bore 66 of the footing 16 without engaging the threaded surface 70 of the footing. The axial length of cylindrical surface 187 is greater than the depth of the bore 66 so that the bearing surface 188 of the distractor may bear against the bottom surface 68 of the footing 16.

Adjacent the distal end 184 of the distracter 18 there is second interengaging means 190 comprising a thread cut into the exterior surface of the distal end 184. The configuration of the thread 190 is complimentary to thread 50 of the fixture 12. The distal end 184 also includes a substantially planar surface 192. The planar surface 192 defines a socket 194.

The distractor 18 also includes an o-ring 196. The o-ring may be made from silicone. The o-ring 196 has an internal diameter just slightly smaller than the diameter D of the distractor 18 so that the o-ring is snugly received on the cylindrical portion 186 of the distractor 18. At the initial stage of use the o-ring 196 is installed on surface 186 slightly axially remote from the reduced cylindrical surface 187. The exterior diameter of o-ring 196 is large enough that the o-ring will engage cylindrical surface 52 and land 54 of the fixture 12 when the distractor is inserted into the fixture 12. This forms a seal for purposes which will be explained below.

In use, the interengaging means 190 of the distracter comprise second interengaging means for engaging with first interengaging means 50 of the fixture 12. Thus, the threads 190 engage the threads 50 for adjustably locating the fixture 12 relative to the distracter 18.

FIG. 6 illustrates the obturator 20. The obturator 20 is substantially symmetrical about an axis 234. The obturator includes a proximal end 236 and a distal end 238. Adjacent the proximal end 236 of the obturator 20 there is a proximal tapered surface 248 which tapers inwardly toward the axis 234. The obturator is a substantially solid body with a proximal surface 242. Adjacent the distal end 238 of the obturator 20 is an interengaging means 252. The interengaging means 252 is in the form of a thread. The configuration of the thread 252 is complimentary to thread 50 of the fixture 12.

Also adjacent the distal end 238 of the obturator 20 there is a substantially planar surface 260. The substantially planar surface 260 defines a socket 262 for receiving a tool to rotate the obturator 20.

Figure 12:
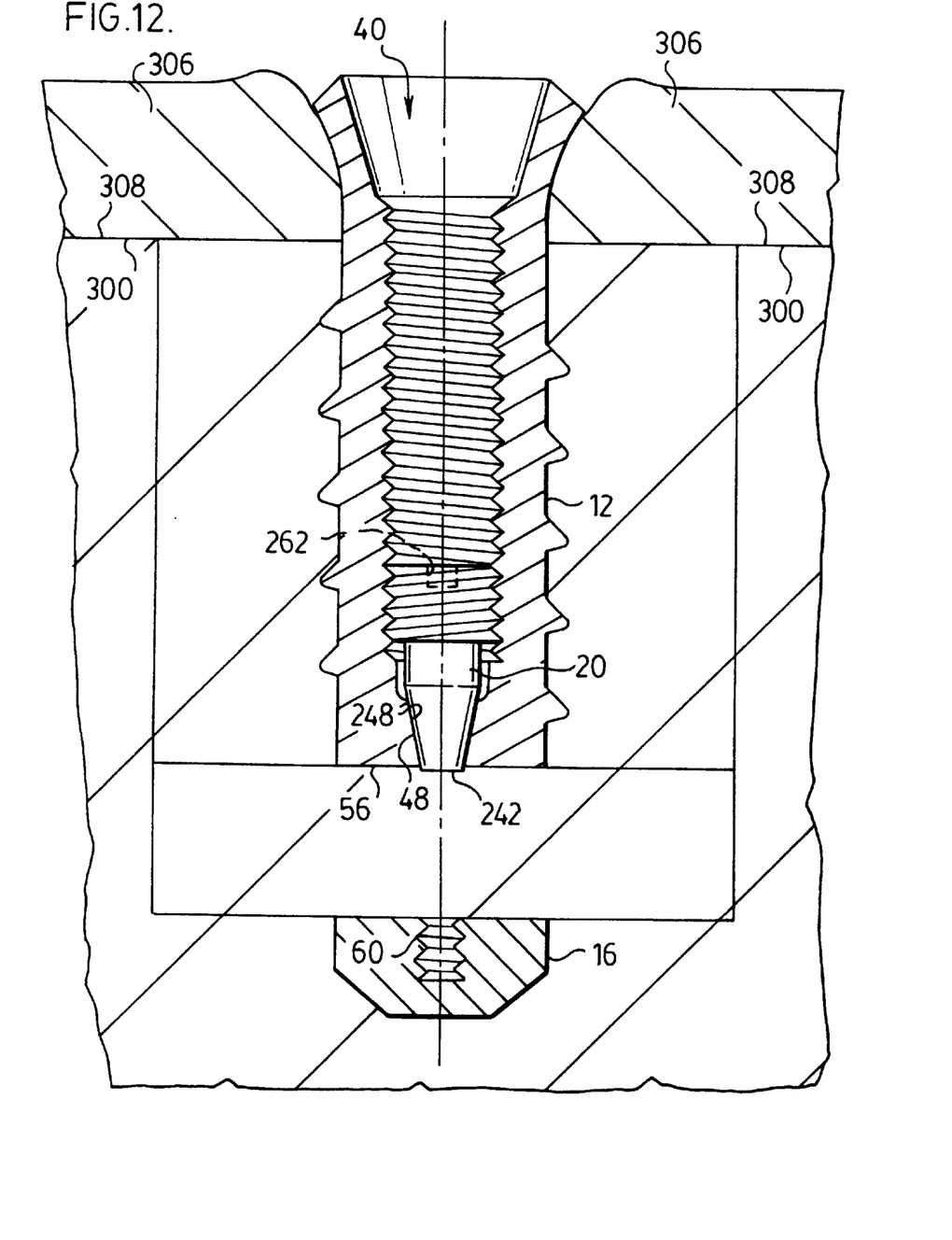
FIG. 12 illustrates the use of the component of FIG. 6 following the distraction procedure.

The obturator 20 may be installed in the fixture 12 as shown in FIG. 12. In order to install the obturator 20 in the fixture 12, the obturator 20 is passed through the distal opening 44 of the fixture 12. The obturator 20 is passed downwardly along the bore 40 of the fixture 12 until such time as the thread 252 begins to engage the thread 50 of the fixture 12. Then by rotating the obturator 20 relative to the fixture 12 by means of a tool inserted in socket 262, the obturator 20 may be rotated and caused to pass downwardly in the bore 40. The obturator 20 will progress axially along the bore 40 until the proximal tapered surface 248 engages the proximal tapered surface 48 of the fixture 12. Preferably, proximal tapered surface 48 of the fixture 12 is what is referred to as a Morse Taper. This is a taper having an effective angle of approximately 8° relative to the axis 34. Corresponding proximal tapered surface 248 of the obturator 20 is thus tightly driven against the tapered surface 248 forming a complete seal between the surfaces 48 and 248.

It is preferable that proximal surface 242 of the obturator 20 be either flush with the proximal surface 56 of the fixture 12 when the tapered surfaces 248 and 48 are in contact with each other. However, in order to provide tolerances it is more preferable that the proximal surface 242 extend in the proximal direction beyond the proximal surface 56 of the fixture 12 for reasons which will be discussed subsequently.

FIGS. 7 through 12 illustrate the use of the components shown in FIGS. 1 through 6 by a surgeon for the process of augmenting bone.

Figure 7:
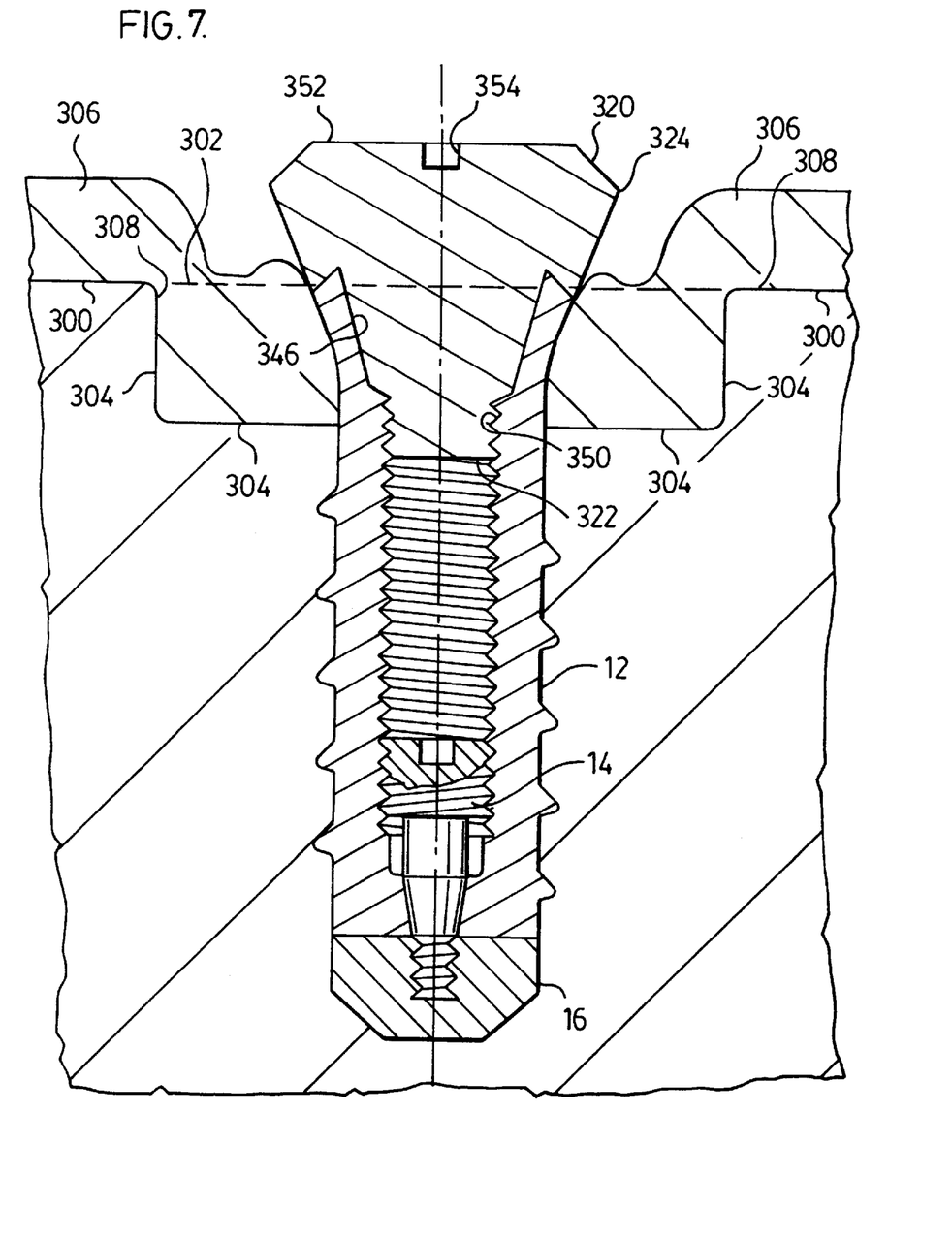
FIG. 7 illustrates the assembly of FIG. 1 when placed in a jaw bone.

FIG. 7 illustrates the assembly of FIG. 1 having been implanted in the jaw bone of a human patient in which there is a need for augmentation of bone. In FIG. 7 a surface of the bone is illustrated at 300. The dotted line 302 illustrates what would be the desired profile of the bone. The line 304 illustrates the profile of bone which is deficient from the desired thickness. The surface 304 may differ from the desired surface 302 for any number of medical conditions. The bone may have been chipped or fractured as a result of impact or other trauma, a portion of the bone may have been required to be removed surgically by reason of disease or other similar condition, or alternatively, the desired bone configuration may not have existed from birth. Whatever the reason for the deviation from the norm, the surgeon desires to augment the bone tissue and to create a solid bone with a surface substantially aligning with line 302 of FIG. 7. In order to achieve this, the components shown in FIGS. 2 through 5 may be utilized to achieve the desired bone augmentation.

The first step is the assembly of the fixture 12, the retaining screw 14 and the footing 16 into the configuration as shown in FIG. 1. As explained previously, the distal surface 60 of the footing 16 is desirably in contact with the proximal surface 56 of the fixture 12. This may be done in the initial manufacturing facility so that the assembly can be presented to the surgeon in a sterile package ready for installation in a desired opening.

The surgeon then creates the desired opening in the bone of the patient. Depending upon the osseointegration mechanism desired, the bone may be configured accordingly. If the osseointegration is to be achieved by use of the rib 58 in the form of a thread as shown on the fixture 12 in FIG. 2, then the bore drilled in the bone by the surgeon will be similarly threaded to receive the rib. Once the assembly of the fixture 12, the retaining screw 14 and the footing 16 is placed within the bone, a healing cap 320 is placed within the fixture 12. The healing cap has a proximal end 322 and a distal end 324. Adjacent the proximal end 322 of the healing cap 320 there is a thread 350. The thread 350 of the healing cap 320 engages the thread 50 of the fixture 12.

The healing cap 320 includes a tapered surface 346 intermediate the proximal and distal ends of the healing cap. The distal end 324 of the healing cap 320 defines a distal surface 352. The distal surface 352 defines a socket 354. The socket 354 is intended to receive a tool for rotating the healing cap 320 relative to the fixture 12. Accordingly, once the assembly of the fixture 12, the retaining screw 14 and the footing 16 has been surgically inserted in the bone, the healing cap 320 is passed into the bore 40 of the fixture 12. A tool is inserted into the socket 354 and the healing cap rotated. The healing cap then seals the distal opening 44 of the fixture 12 by bringing tapered surface 346 of the healing cap into contact with the distal tapered surface 46 of the fixture 12. The appropriate layers overlying the bone, namely the mucosa 306 and the periosteum 308 are then placed by the surgeon adjacent them healing cap. When the assembly as shown in FIG. 7 is completely installed, the proximal surface 62 of the footing 16 bears against the bottom of the cavity made by the surgeon in the jaw bone. The wound is then temporarily closed and permitted to heal. The normal healing pace typical of other dental implants is then allowed to occur. Osseointegration then occurs between the bone and the external surface 32 of the fixture 12 as well as the proximal surface 62 of the footing 16. For most human patients this would require a healing period from four to six months. During this period no distraction osteogenesis occurs.

During the period of osseointegration it is desirable that no bodily fluids enter the surgical implantation site through the fixture. The bore 40 of the fixture 12 is sealed during this healing phase by the interaction of tapered surfaces 48 and 87 of the fixture 12 and the retaining screw 14. In addition, the bore 40 is sealed at the distal end by tapered surface 346 of the healing cap 220 and tapered surface 46 of the fixture 12. Similarly, it is desirable that fluids from the implantation site do not enter between surfaces 60 and 56 of the footing 16 and fixture 12 respectively. For this reason, the footing 16 is tightened on threaded surface 86 of the retaining screw in the initial assembly at the manufacturing facility so that the two surfaces are in intimate contact.

Figure 8:
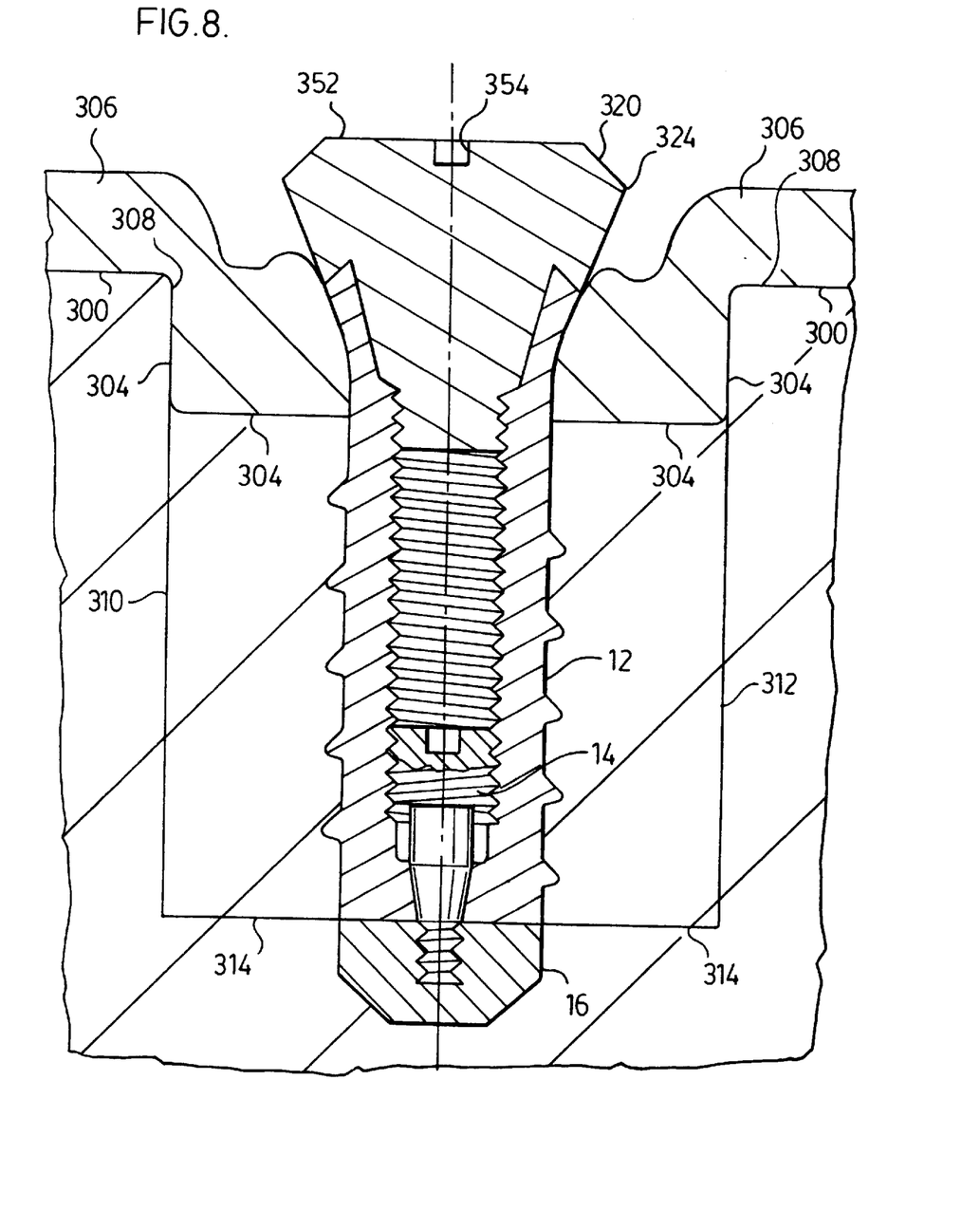
FIG. 8 illustrates the site of the surgical procedure to be performed after placement of the device as shown in FIG. 7.

When the surgeon determines that sufficient osseointegation of the fixture 12 and the footing 16, have occurred, the surgeon is then ready to commence the distraction osteogenesis process. In order to carry out the distraction osteogenesis, the surgeon then opens the original site of implantation so as to have access to the site where bone augmentation is desired. The surgeon then performs a corticotomy as shown in FIG. 8. The lines marking the cuts made in the bone are shown in FIG. 8 as 310 and 312 on either lateral side of the implant. The lines 310 and 312 are laterally displaced on either side of the fixture 12 as desired for the required bone augmentation. In addition, a proximal cut is made along the line indicated by 314 in FIG. 8.

Once the corticotomy has been performed, the healing cap 320 is removed and the retaining screw 14 is removed from the footing 16 and from the fixture 12 by rotating the retaining screw 14. In order to remove the screw, a tool is inserted into the socket 94 of the retaining screw 14. As the retaining screw is turned it will turn in the threads 50 of the fixture 12 and the threads 70 of the footing. To permit this to occur the threads 70 and the threads 50 have the same pitch. Because of the osseointegration process, the fixture 12 and the footing 16, which by this time have become integrated with the bone, do not rotate. The retaining screw 14 however has been maintained in place throughout the healing process after the initial implantation procedure. This ensures that the footing 16 remains in contact with the fixture 12 and aligned so that the bore 66 of the footing and the bore 40 of the fixture remain exactly aligned.

Figure 9:
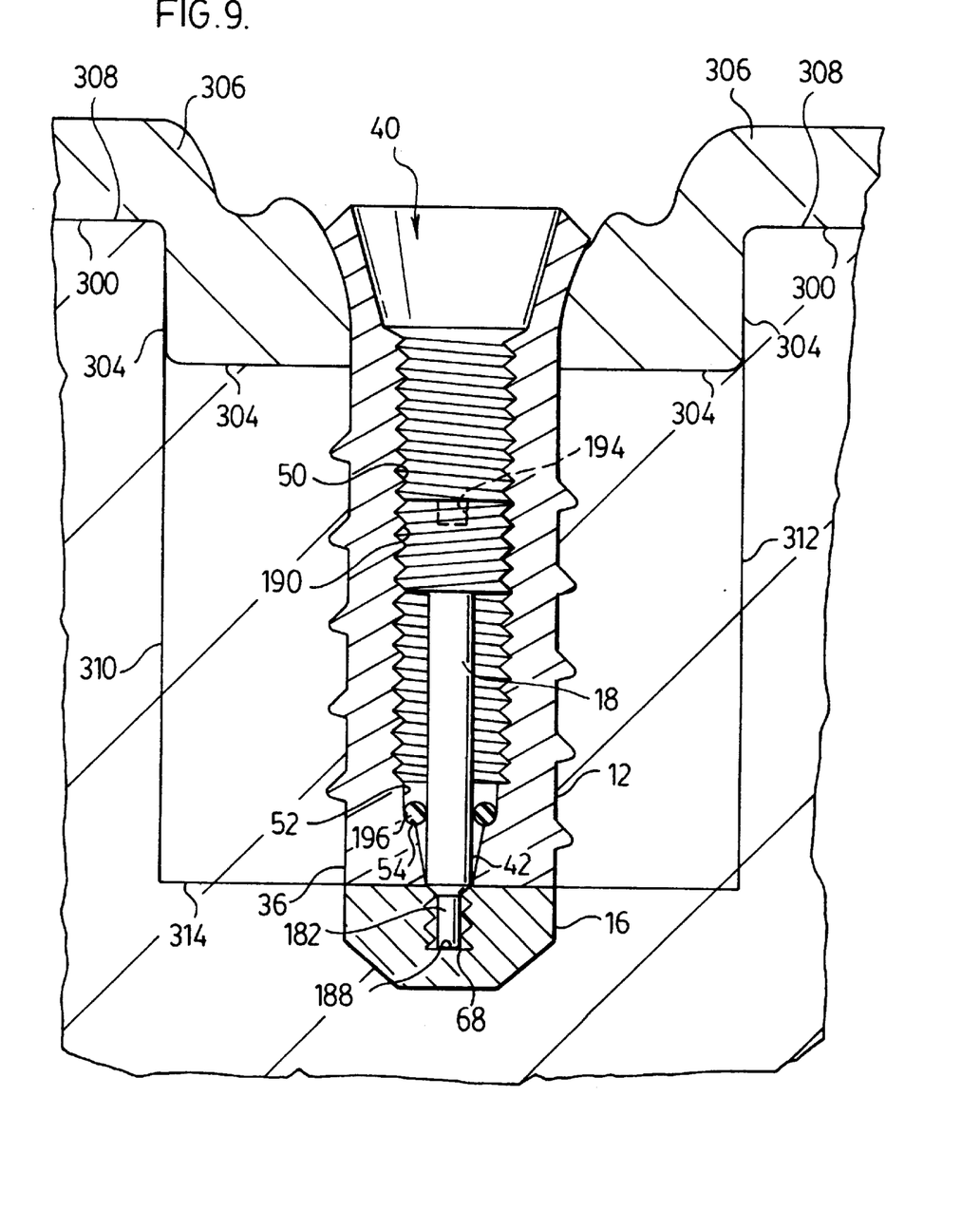
FIG. 9 illustrates the assembled components of FIGS. 2, 3 and 5 at the beginning of the distraction stage.

FIG. 9 illustrates the commencement of the distraction procedure. In order to commence the distraction procedure, the distracter 18 is placed within the fixture 12. A tool is inserted into the socket 194 of the distracter 18. The distracter 18 is then placed within the bore 40 with the proximal end 182 approaching the proximal end 36 of the fixture 12. Rotation of the distracter 18 engages the thread 190 with the thread 50 of the fixture, thus causing the distracter 18 to pass downwardly along the bore 40. As the distracter advances along the bore 40, the proximal end 182 passes through the proximal opening 42 of the fixture 12 toward the footing 16. The distracter continues to advance along the bore 40 of the fixture 12 until the bearing surface 188 of the distracter bears against the footing 16. In the preferred embodiment, the proximal end 182 of the distractor 18 enters into the bore 66 and contacts the bottom surface 68 of the bore of the footing. Because the footing 16 is osseointegrated with the bone, the distracter 18 cannot move downwardly as it will then bear against the footing which is firmly integrated into the bone tissue. Further turning of the distracter will not result in any movement in the direction of distraction between the distracter 18 and the footing 16. However, because the thread 50 of the fixture 12 and the thread 190 of the distracter 18 remain engaged, further rotation of the distracter 18 relative to the footing 16 and the fixture 12 results in the fixture moving in the distal direction relative to the footing 16. Movement of the fixture 12 relative to the footing 16 then establishes the direction of distraction. When the distractor 18 is shipped from the manufacturing facility, preferably the o-ring 196 will have been installed as shown in FIG. 5. Alternatively, the surgeon will install the o-ring 196. When the distractor 18 is installed in the fixture 12, the o-ring 196 will bear against surface 52 at the land 54.

Following the corticotomy, the fixture 12 is firmly integrated in a segment of bone which is defined by the corticotomy cuts 310, 312 and 314. That segment of bone cannot rotate relative to surrounding tissues. Thus, the segment of bone into which the fixture 12 is integrated will be caused to move in the direction of distraction.

As illustrated in the work of Illizarov referred to above, it is known that new bone tissue will generate along the incision cut 314 as well as along the cuts 310 and 312. Final bone healing will not occur along cuts 310 and 312 as, through the procedure, movement is occurring along these cuts faster than healing will occur and the healing will occur when movement or distraction no longer occurs and the bone is held in a stabilized position.

To perform the distraction osteogenesis, the distracter 18 is rotated on a regular basis a small amount. This may involve turning the distracter 18 a small amount (such as one turn) on a daily basis so that the separation from the cut 314 is increased by an amount of about ½ to 1 mm on a daily basis.

The fixture 12 and the bone segment in which it is embedded are thus caused to move in the direction of distraction a total amount as determined by the surgeon. As the fixture 12 moves away from the footing 16, body fluids can flow between surfaces 60 of the footing 16 and 56 of the fixture to generate new bone growth. It is desirable that those fluids not enter into the bore 40 of the fixture as necrosis may occur and it is desirable that no bacteria or other fluids pass down through the bore 40 into the site of bone regeneration. The o-ring 196 provides the desired seal. The healing cap 320 may also be reinstalled each day to assist in sealing. As the fixture 12 rises in FIG. 9 relative to the distractor 18, the o-ring 196 remains in contact with surface 52 and the land 54 of the fixture. The o-ring is rolled along the cylindrical surface 186 of the distractor.

Figure 10:
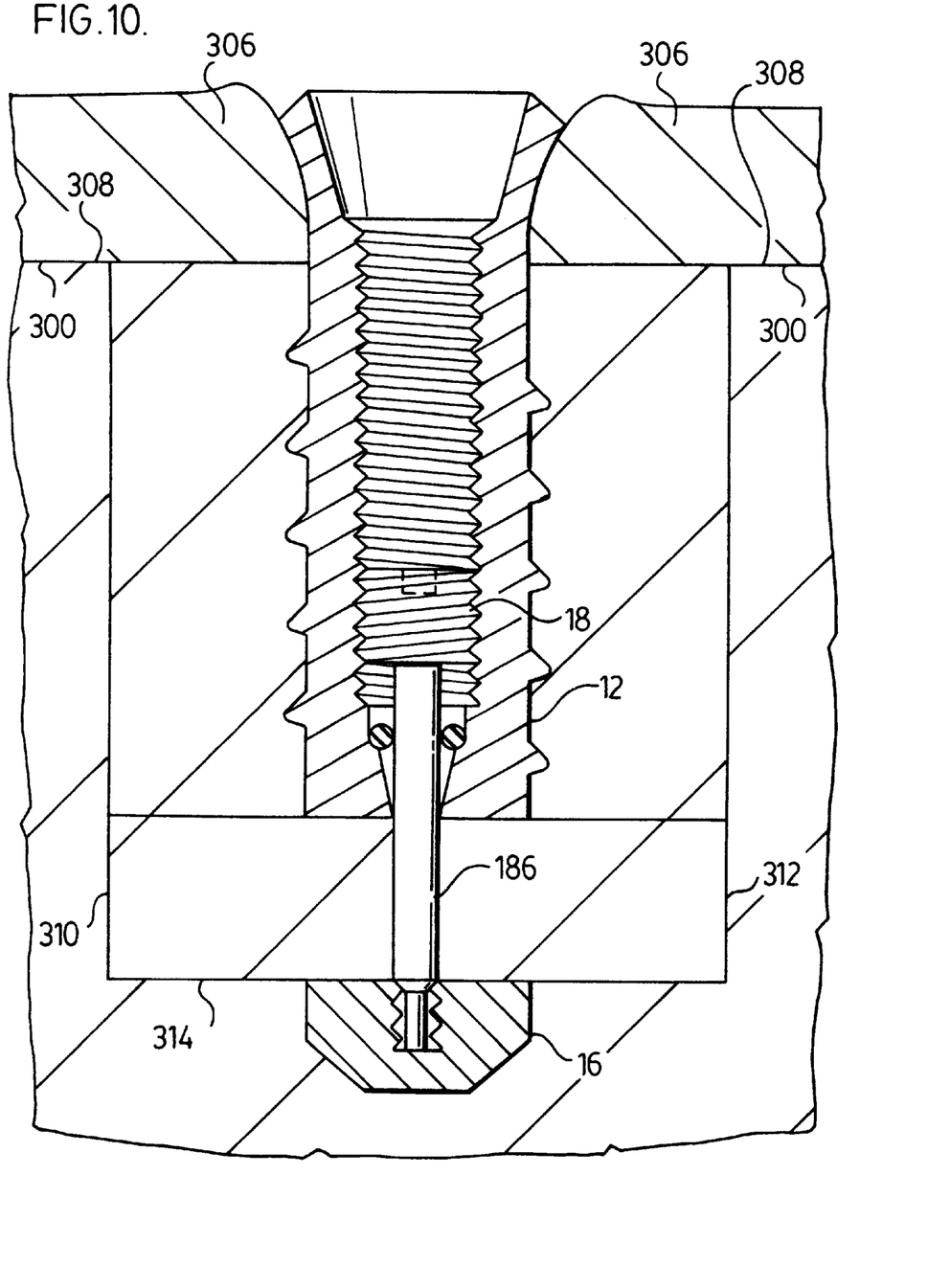
FIG. 10 shows the components of FIG. 9 at the completion of the distraction stage.

FIG. 10 illustrates the procedure when the desired amount of distraction has occurred. As shown in FIG. 10, the surface of the bone segment integrated with the fixture 12 has been moved to approximate the line 302 shown in FIG. 7. Depending upon the length of travel along the direction of distraction, one or more distracters of different length may be used. If significant travel in the direction of distraction relative to the length of the fixture 12 is desired, it may be desirable or necessary to use a number of distracters. In each case the length of the cylindrical portion 186 suits the amount of distraction travel and distance from footing 16 as required.

Figure 11:
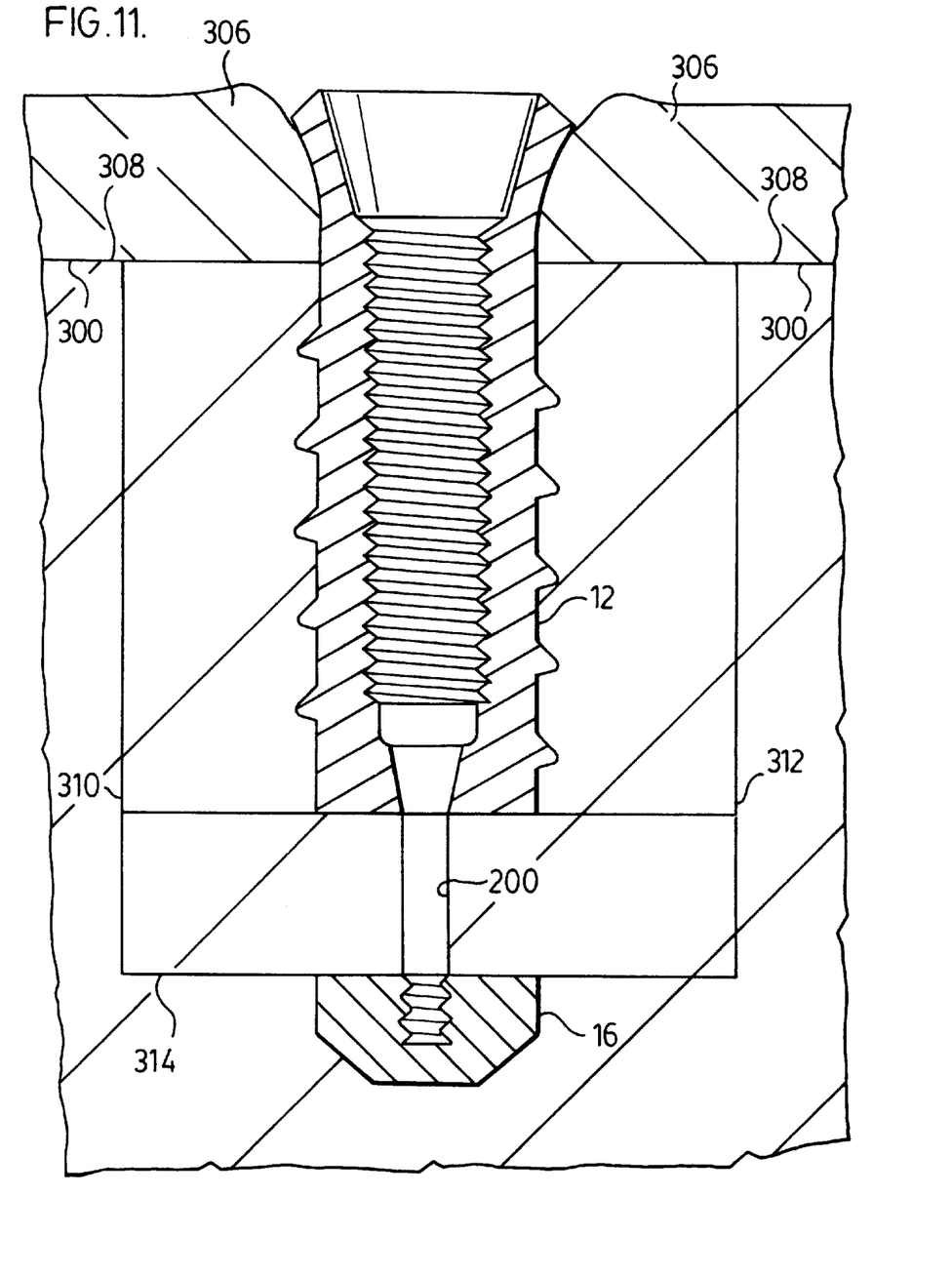
FIG. 11 shows the components of FIG. 10 after removal of the component of FIG. 5.

The procedure of distraction osteogenesis is completed as shown in FIG. 10. The next step in the procedure is to allow healing to occur at the side edges of the distracted bone segment. Healing will naturally occur as long as no movement occurs between the distracted segment and the surrounding bone. To promote proper healing, the distracted segment is stabilized. This may be done using the distractor 18 or by external support such as a bridge. Thereafter, the distracter 18 and the o-ring 196 are removed as shown in FIG. 11. With removal of the distracter 18 there will remain a cylindrical void in the newly formed bone which has been created during the osteogenesis process.

During the osteogenesis phase body fluids will surround the cylindrical portion 186 of the distractor 18. Obviously, it is not desirable to have any osseointegration occur along the surface 186 of the distractor 18. Accordingly, this surface is as smooth as possible and the distractor 18 is made from a material which will be tolerated by the body but which does not promote osseointegration. Advantageously, the distractor may be made from stainless steel.

In order to prevent infection in the bone from occurring, the obturator 20 is then placed within the fixture 12. By and large, it is desirable to ensure that bodily fluids do not have an easy path into the interior of the bone which has been generated by the distraction process. Thus, it is desirable to seal the proximal opening 42 of the fixture 12 on completion of the distraction procedure. To accomplish this, a tool is inserted into a socket 262 of the obturator 20. The obturator 20 is then passed along the bore 40 of the fixture until the thread 252 of the obturator 20 engages the thread 50 of the fixture. The obturator 20 is then rotated to pass along the bore 40 until the tapered surface 248 engages with the proximal tapered surface 48 of the fixture 12. The Morse Taper then creates a permanent seal preventing the passage of any fluids through the bore 40 into the newly generated bone. This is shown in FIG. 12.

With the passage of time, the cylindrical void in the regenerated bone which is created by removal of the distractor 18, will be filled in spontaneously with bone tissue. In addition, the bore 60 of the footing 16 will be filled in by bone tissue.

The void which was formerly occupied by the cylindrical portion 186 of the distractor is surrounded by newly created bone tissue. This void will thus develop bony tissue relatively readily. It is desirable however that there be no void extending into the bore of the fixture 12 when the obturator 20 is installed within the bore 40 of the fixture. Thus, desirably the obturator is dimensioned so that when the tapered surface 248 of the obturator engages with tapered surface 48 of the fixture 12, the proximal surface 242 of the obturator extends axially outwardly of the bore 40. Thus, the surface 242 of the obturator 20 will be below the surface 56 of the fixture 12. Thus, prior to filling in of the void, the obturator 20 will project slightly into the cylindrical void.

This will ensure that there is no void adjacent the distal opening 42 which might otherwise be a possible site for potential necrosis.

Figure 13:
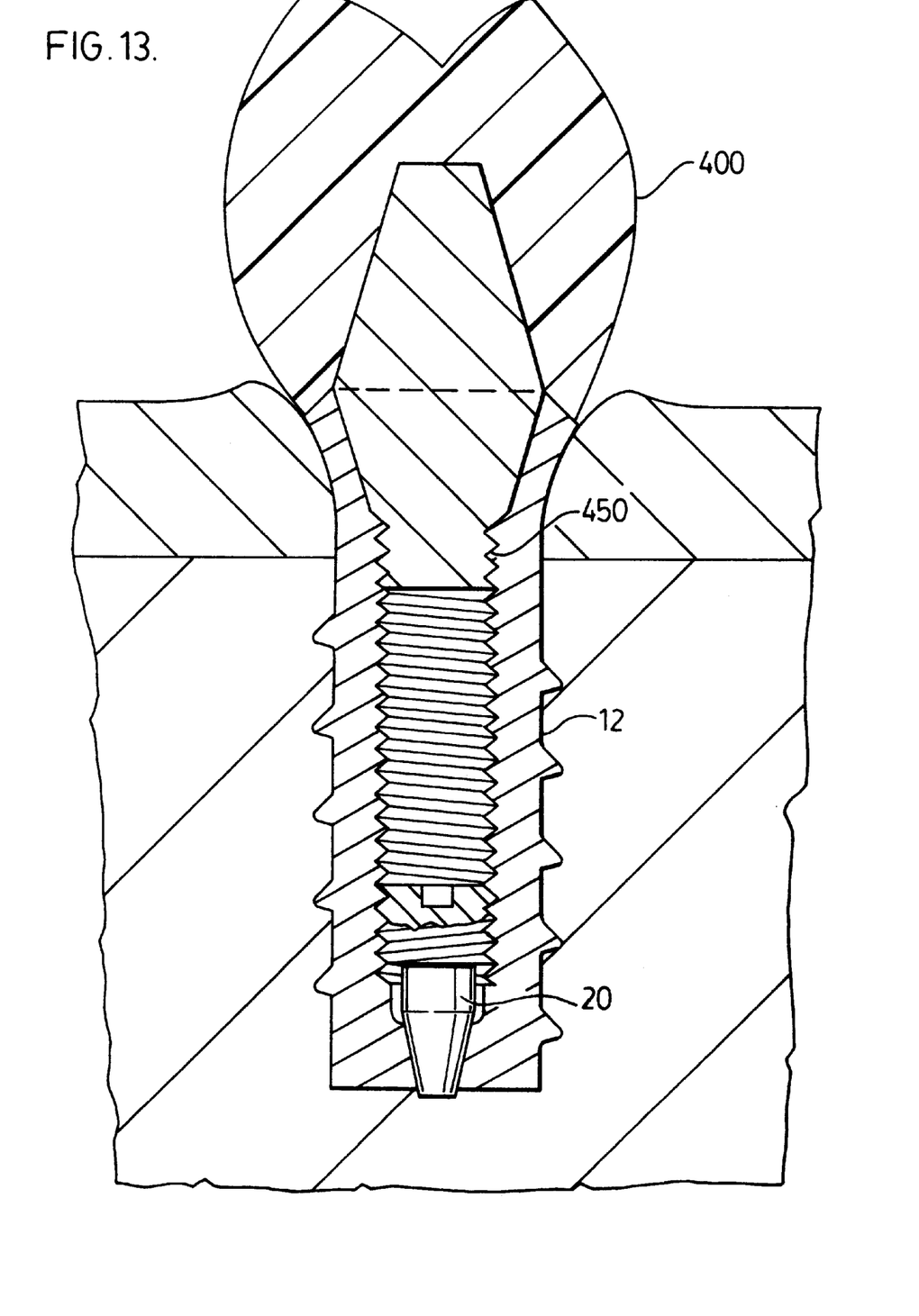
FIG. 13 illustrates the use of the components of FIG. 12 after healing is completed.

Upon completion of the osteogenesis procedure, the fixture 12 may remain in place having been firmly integrated in the bone tissue. The sides of the segment of bone which has been moved in the direction of distraction which were originally created by the cuts along lines 310 and 312 will become healed to adjacent bone with the passage of time. The fixture 12 remains in place where it can now be used to serve as an anchor for whatever may be desired. In the case of augmentation of a jaw bone as shown in FIG. 13, it may be desirable or necessary to provide a prosthesis 400 which is anchored to the jaw bone. The prosthesis is manufactured with a thread 450 which can engage with the thread 50 of the fixture 12.

The material from which the various components are manufactured is a matter of choice. It is intended that the fixture 12 and the obturator 20 remain permanently in the body in most situations. Thus, these should be manufactured from materials which are suitable for osseointegration and which will be tolerated by the body on a long term basis. Such materials include titanium, or titanium alloys.

There will be no access to the footing 16 after completion of the osteogenesis process. Thus, the footing 16 may be manufactured from a material similar to the fixture 12, that is a material which promotes osseointegration and which can be tolerated by the body on a long term basis such as titanium or titanium alloy. Alternatively, the footing may be manufactured from a material which may be biologically absorbed by the body. Such materials include calcium carbonate and polylactic/polyglycolic acid polymer known as PGLA.

The retaining screw 14 will not be osseointegrated with the body and for the most part will not be in contact with bodily fluids. The retaining screw may thus be manufactured from any material which will be tolerated by the body over the period of several months between the original implantation and the commencement of the distraction process. Such materials include titanium, titanium alloy, stainless steel and gold alloy.

It is desirable that there is as little integration between the distractor and surrounding bone as possible. The distractor is, however, subject to contact by bodily fluids, particularly at the site of osteogenesis. The distractor does, however, have certain structural requirements as it effectively provides the jacking connection between the footing and the fixture. The distractor may advantageously be manufactured from stainless steel or gold alloys.

While the invention has been discussed in the context of the preferred embodiment it will be apparent that various modifications may be made. In particular, the interengaging means of the fixture and the various components need not be in the form of a single thread but could be in other forms such as multiple threads, bayonet and slot connectors, pins and holes or gears and racks. The components may be made of various materials which are acceptable to the body of the mammal. Other types of sealing means including gaskets, serpentine seals and other types of seals may be employed to seal the bore of the fixture as indicated. The shape of the components may be varied. The scope of the invention is not limited to the embodiment shown herein, but rather by the scope of the attached claims.

We claim:

1. A kit of assemblable components for implantation into the bone of a mammal for use in distraction osteogenesis comprising:

a fixture, a footing and a distracter, said fixture comprising a longitudinally extending body portion with a proximal end and a distal end, said body portion having an exterior surface adapted for contact and integration with bone tissue, said body portion having a generally longitudinally extending bore extending from a proximal opening adjacent said proximal end to a distal opening adjacent said distal end, said footing comprising a proximal surface and a distal surface, said distracter comprising a generally rod-shaped body including a distal end and a proximal end, and said proximal end of said distracter adapted to bear against said footing, and first and second interengaging means on said fixture and said distracter respectively for adjustably locating said fixture relative to said distracter, said distracter having a length so that the distal end of said distracter is within said bore of said fixture when said proximal end of distracter bears against said footing, and said fixture having a sealing surface adjacent said distal end of said bore of said fixture for sealing said bore during distraction.

2. The kit of assemblable components of claim 1 said device further comprising a retaining screw.

3. The kit of assemblable components of claim 2, wherein said footing comprises a bore extending from said proximal surface into said footing and said proximal end of said distracter is adapted to fit within said bore of said footing.

4. The kit of assemblable components of claim 3, wherein said retaining screw is adapted to be received within said bore of said fixture and within said bore of said footing.

5. The kit of assemblable components of claim 4, wherein said retaining screw comprises interengaging means for interengaging with said interengaging means of said fixture for adjustably locating said retaining screw relative to said fixture.

6. The kit of assemblable components of claim 5, wherein said first interengaging means of said fixture comprises a thread and said interengaging means on said retaining screw comprises a first complimentary thread.

7. The kit of assemblable components of claim 6, said retaining screw comprising a second thread, said retaining screw having a proximal end and a distal end, said second thread located at said proximal end of said screw, and said first and second threads have equal pitch.

8. The kit of assemblable components of claim 7 wherein said bore of said footing comprises a thread adapted to receive said second thread of said retaining screw.

9. The kit of assemblable components of claim 8 wherein said fixture comprises a tapered surface adjacent said proximal end of said fixture, said retaining screw comprises a tapered surface for sealing against said tapered surface of said fixture.

10. The kit of assemblable components of claim 9, said retaining screw having a length sufficient that when said tapered surface of said retaining screw engages said tapered surface of said fixture, said proximal end of said retaining screw extends through said proximal opening of said fixture, so that said footing may be threaded onto said retaining screw.

11. The kit of assemblable components of claim 10, said fixture having a proximal surface, and said bore of said footing is sufficiently long that said footing may be retained on said retaining screw when said retaining screw is sealed against said fixture, with said distal surface of said footing in contact with said proximal surface of said fixture.

12. The kit of assemblable components of claim 2, further comprising an obturator adapted to be received within said bore of said fixture for plugging said bore of said fixture.

13. The kit of assemblable components of claim 12, wherein said obturator comprises an interengaging means for adjustably locating said obturator relative to said fixture.

14. The kit of assemblable components of claim 13, said obturator having a proximal end and a distal end; said obturator having a tapered surface adjacent said proximal end for sealing against said bore of said fixture.

15. The kit of assemblable components of claim 14, said fixture having a tapered surface adjacent said proximal opening and said tapered surface of said obturator seals against said tapered surface of said fixture.

16. The kit of assemblable components of claim 15, wherein said interengaging means of said fixture is a thread and said obturator comprises a complementary thread.

17. The kit of assemblable components of claim 2 wherein said first interengaging means on said fixture comprises a thread and said second interengaging means on said distracter comprises a complementary thread.

18. The kit of assemblable components of claim 17, wherein said distracter comprises a first generally cylindrical portion having a diameter D, said first cylindrical portion extending to adjacent said proximal end of said distracter.

19. The kit of assemblable components of claim 18, wherein said distracter comprises a second generally cylindrical portion at said proximal end of said distracter; said second cylindrical portion having a diameter which is less than said diameter D.

20. The kit of assemblable components of claim 19, wherein said bore of said footing comprises a thread and said second cylindrical portion of said distracter has a diameter less than the diameter of said thread of said bore of said footing.

21. The kit of assemblable components of claim 20, wherein said distracter comprises an o-ring.

22. The kit of assemblable components of claim 21, wherein said o-ring is adapted to be snugly received on said first generally cylindrical portion with diameter D.

23. The kit of assemblable components of claim 22, wherein said bore of said fixture comprises a tapered surface adjacent said proximal opening.

24. The kit of assemblable components of claim 23, wherein said bore of said fixture comprises a generally cylindrical portion, said generally cylindrical portion merging into said tapered surface at a land.

25. The kit of assemblable components of claim 24, wherein said o-ring of said distracter is adapted to bear against said land of said generally cylindrical portion of said bore of said fixture when said distracter is fitted within said bore of said fixture.

26. A kit of assemblable components for implantation into the bone of a mammal for use in distraction osteogenesis comprising:

a fixture, a footing, a distracter, an obturator, a healing cap and a retaining screw, said fixture comprising a longitudinally extending body portion with a proximal end and a distal end, said body portion having an exterior surface adapted for contact and integration with bone tissue, said body portion having a generally longitudinally extending bore extending from a proximal opening adjacent said proximal end to a distal opening adjacent said distal end, said footing comprising a proximal surface and a distal surface, said fixture having first interengaging means within said bore of said fixture, each of said distracter, obturator and retaining screw having interengaging means for co-operating with said first interengaging means of said fixture for adjustably locating said fixture relative to said distracter, obturator and retaining screw, said footing including a bore extending from said distal surface, said bore having a thread, said retaining screw including a thread for cooperating with said thread of said footing, said distracter having a proximal end and said proximal end of said distracter is adapted to bear against said footing and said distracter having a length so that the distal end of said distracter is within said bore of said fixture when said proximal end of distracter bears against said footing, and said fixture having a sealing surface adjacent said distal end of said bore of said fixture for sealing said bore during distraction.

27. The kit of assemblable components of claim 26 wherein said first interengaging means and said interengaging means of said distracter, obturator and retaining screw are threads, and said threads of said first interengaging means and said threads of said bore of said footing have the same pitch.

28. The kit of assemblable components of claim 27 wherein said bore of said fixture comprises a tapered surface, and said obturator and said retaining screw comprises a co-operating tapered surface for respectively sealing against said tapered surface of said bore.

29. The kit of assemblable components of claim 28 wherein said components are assemblable into an implant for insertion into a jaw of said mammal.

30. The kit of assemblable components of claim 29 wherein said fixture is adapted to serve as a permanent implant in said jaw.

31. The kit of assemblable components of claim 30 further including a prosthesis, said prosthesis having a thread for attachment of said prosthesis to said fixture adjacent said distal end of said fixture.

* * * * *

UNITED STATES PATENT AND TRADEMARK OFFICE
CERTIFICATE OF CORRECTION

PATENT NO.    : 6,126,662
DATED         : October 3, 2000
INVENTOR(S)   : Robert P. Carmichael, George K.B. Sandor and Donald R. Johnson It is certified that error appears in the above-identified patent and that said Letters Patent is hereby corrected as shown below:

Column 12,
Line 29, commencing with "said footing comprises...." and ending with "....extending from said proximal", delete line 29 entirely and replace with:
-- said footing comprises a bore extending from said distal --

Signed and Sealed this

Seventeenth Day of September, 2002

*Attest:*

JAMES E. ROGAN
*Attesting Officer*              *Director of the United States Patent and Trademark Office*